United States Patent
Christensen

(10) Patent No.: US 9,671,332 B2
(45) Date of Patent: Jun. 6, 2017

(54) MINIATURE TUNABLE LASER SPECTROMETER FOR DETECTION OF A TRACE GAS

(71) Applicant: California Institute of Technology, Pasadena, CA (US)

(72) Inventor: Lance E. Christensen, Baldwin Park, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 14/162,578

(22) Filed: Jan. 23, 2014

(65) Prior Publication Data

US 2014/0204382 A1 Jul. 24, 2014

Related U.S. Application Data

(60) Provisional application No. 61/755,832, filed on Jan. 23, 2013.

(51) Int. Cl.
*G01N 21/25* (2006.01)
*G01N 21/39* (2006.01)
(Continued)

(52) U.S. Cl.
CPC ........... *G01N 21/39* (2013.01); *G01N 21/031* (2013.01); *G01N 21/3504* (2013.01);
(Continued)

(58) Field of Classification Search
CPC .. G01N 21/3504; G01N 21/39; G01N 21/031; G01N 2021/399; G01J 3/42; G01J 3/26
(Continued)

(56) References Cited

U.S. PATENT DOCUMENTS 4,035,083 A * 7/1977 Woodriff .................. G01J 3/28
250/225
5,177,566 A * 1/1993 Leuchs ................ G01B 9/0207
356/43
(Continued)

FOREIGN PATENT DOCUMENTS

WO WO 02/073757 A2 9/2002
WO WO 2006/007446 A2 1/2006
(Continued)

OTHER PUBLICATIONS

Herman, et al., JPL Laser Hygrometer (JLH) for in-situ water vapor measurements, Jet Propulsion Laboratory, California Institute of Technology, 2012, 1 page.
(Continued)

*Primary Examiner* — Tarifur Chowdhury
*Assistant Examiner* — Mohamed K Amara
(74) *Attorney, Agent, or Firm* — Lewis Roca Rothgerber Christie LLP

(57) ABSTRACT

An open-path laser spectrometer (OPLS) for measuring a concentration of a trace gas, the OPLS including an open-path multi-pass analysis region including a first mirror, a second mirror at a distance and orientation from the first mirror, and a support structure for locating the mirrors, a laser coupled to the analysis region and configured to emit light of a wavelength range and to enable a plurality of reflections of the emitted light between the mirrors, a detector coupled to the analysis region and configured to detect a portion of the emitted light impinging on the detector and to generate a corresponding signal, and an electronic system coupled to the laser and the detector, and configured to adjust the wavelength range of the emitted light from the laser based on the generated signal, and to
(Continued)

measure the concentration of the trace gas based on the generated signal.

20 Claims, 6 Drawing Sheets

(51) Int. Cl.
    *G01N 21/3504*     (2014.01)
    *G01N 21/03*     (2006.01)

(52) U.S. Cl.
    CPC ............... *G01N 2021/3513* (2013.01); *G01N 2021/399* (2013.01); *G01N 2201/0221* (2013.01)

(58) Field of Classification Search
    USPC ............ 356/432, 440, 73, 454; 250/339.13; 73/23.2, 23.37
    See application file for complete search history.

(56) References Cited

U.S. PATENT DOCUMENTS

| | | | | |
|---|---|---|---|---|
| 5,764,678 A * | 6/1998 | Tada | ............. | H01S 3/03 372/107 |
| 6,570,159 B2 | 5/2003 | Ankerhold | | |
| 6,643,018 B2 | 11/2003 | Chavanne | | |
| 6,713,754 B1 * | 3/2004 | Mueller | ............. | G03B 27/73 250/226 |
| 6,753,960 B1 * | 6/2004 | Polynkin | ............. | G01J 3/02 356/330 |
| 7,174,099 B1 * | 2/2007 | Chinn | ............. | H04B 10/564 372/29.01 |
| 7,830,926 B1 * | 11/2010 | Kim | ............. | B82Y 20/00 372/20 |
| 2003/0043378 A1 | 3/2003 | DiDomenico et al. | | |
| 2003/0095736 A1 * | 5/2003 | Kish, Jr. | ............. | B82Y 20/00 385/14 |
| 2003/0231665 A1 * | 12/2003 | Ichino | ............. | H01S 5/042 372/32 |
| 2004/0151438 A1 * | 8/2004 | Ferguson | ............. | G02B 6/264 385/78 |
| 2006/0039009 A1 * | 2/2006 | Kiesel | ............. | G01J 9/0246 356/519 |
| 2006/0237657 A1 * | 10/2006 | Gamiles et al. | ............. | 250/372 |
| 2007/0246653 A1 * | 10/2007 | Zhou | ............. | 250/339.1 |
| 2007/0273882 A1 * | 11/2007 | Smith | ............. | 356/437 |
| 2008/0062404 A1 * | 3/2008 | Kawano | ............. | G01J 5/08 356/73 |
| 2011/0051772 A1 * | 3/2011 | Fukuda | ............. | B82Y 20/00 372/50.11 |
| 2011/0228275 A1 * | 9/2011 | Xia | ............. | G01N 21/77 356/437 |
| 2011/0251800 A1 * | 10/2011 | Wilkins | ............. | 702/24 |
| 2011/0285998 A1 * | 11/2011 | Hara et al. | ............. | 356/437 |
| 2013/0130400 A1 * | 5/2013 | Harbers | ............. | G01J 3/28 436/171 |
| 2013/0211218 A1 * | 8/2013 | Suzuki | ............. | A61B 5/1455 600/328 |
| 2013/0317372 A1 * | 11/2013 | Eberle | ............. | G01L 1/246 600/478 |
| 2013/0321802 A1 * | 12/2013 | Imura | ............. | G01J 3/0297 356/306 |
| 2014/0085632 A1 * | 3/2014 | Preston | ............. | G01J 3/0205 356/326 |

FOREIGN PATENT DOCUMENTS

| | | | | |
|---|---|---|---|---|
| WO | WO 2010/053612 A1 | 5/2010 | | |
| WO | WO 2010/070147 A1 | 6/2010 | | |
| WO | WO2013119320 | * | 8/2013 | ............ G01N 21/00 |

OTHER PUBLICATIONS

Park et al., Development of the detection system of methane leakage using 3.2 μm mid-infrared LED and PD, 4 pages.

Khan, et al., Low power greenhouse gas sensors for unmanned aerial vehicles, Remote Sensing, May 9, 2012, pp. 1355-1368, vol. 4.

Tarsitano, et al., Multilaser herriott cell for planetary tunable laser spectrometers, Optical Society of America, Oct. 2007, pp. 6923-6935, vol. 46, No. 28.

International Search Report, dated Apr. 28, 2014, and mailed May 1, 2014, corresponding to PCT/US2014/012766, 3 pages.

Written Opinion of the International Searching Authority, dated Apr. 28, 2014, and mailed May 1, 2014, corresponding to PCT/US2014/012766, 3 pages.

Herriott, Donald R., et al. "Folded Optical Delay Lines." *Applied Optics*. vol. 4, No. 8. Aug. 1965: 883-891.

EPO Search Report and Opinion dated Oct. 28, 2016 in corresponding European Patent Application EP14743786 (14 pages).

Christensen et al., "Aircraft and balloon in situ measurements of methane and hydrochloric acid using interband cascade lasers", Applied Optics, 2007, 46(7), pp. 1132-1138.

Christensen et al., "Thermoelectrically cooled interband cascade laser for field measurements", Optical Engineering, 2010, 49(11), pp. 111119-1-111119-6.

Massie et al., "Design of a portable optical sensor for methane gas detection", Sensors and Actuators B: Chemical: International Journal Devoted to Research and Development of Physical and Chemical Transducers, Elsevier BV, NL, 2006, 113(2), pp. 830-836 (Abstract).

Sonnenfroh et al., "Interband cascade laser-based sensor for ambient $CH_4$", Optical Engineering, 2010, 49(11), pp. 111118-1-111118-10.

* cited by examiner

MINIATURE TUNABLE LASER SPECTROMETER FOR DETECTION OF A TRACE GAS

CROSS-REFERENCE TO RELATED APPLICATION(S)

This application claims priority to and the benefit of U.S. Provisional Application No. 61/755,832, filed Jan. 23, 2013, the entire content of which is incorporated herein by reference.

STATEMENT REGARDING FEDERALLY SPONSORED RESEARCH OR DEVELOPMENT

The invention described herein was made in performance of work under a NASA contract, and is subject to the provisions of Public Law 96-517 (35 U.S.C. 202) in which the contractor has elected to retain title.

FIELD

The present invention is directed to a spectrometer, more particularly, to a tunable laser spectrometer for detecting a trace gas, and methods of detecting the same.

BACKGROUND

A known and promising technique for measuring molecular pollutants is laser spectroscopy. The technique, which uses a tunable and narrow linewidth laser light source, offers sensitive and selective detection of trace gases in the infrared (IR) spectral region.

Laser spectrometers use radiation passing through a volume of gas to detect a trace gas. As the radiation passes through the gas, some of its energy is absorbed by the gas at certain wavelengths. The range of wavelengths at which a trace gas exhibits characteristic absorption depends on the properties of the trace gas. For example, methane ($CH_4$) strongly absorbs wavelengths of about 3.2 µm to about 3.5 µm, while carbon monoxide absorbs wavelengths from about 4.2 µm to about 4.5 µm. The level of energy absorption at the absorption wavelengths may be used to determine the concentration of a trace gas.

Recent developments in IR laser light sources radiating in the 3 µm to 10 µm wavelength range show great promise as nearly all molecules of trace gasses have characteristic absorption bands within this region.

Laser spectrometers may be used to detect a plethora of gasses including hydrocarbons, water vapor, and even calcium fluoride. Laser spectrometers are conventionally used in wastewater treatment facilities, refineries, gas turbines, chemical plants, mines, gas distribution lines, and other locations where flammable or combustible gasses may exist, as well as in atmospheric research.

However, current solutions have many shortcomings. Conventional laser spectrometers often use, for example, Quantum cascade (QC) lasers, which suffer from low conversion efficiency (and, thus, have high power consumption) and require heavy and expensive cooling mechanisms. Furthermore, commercial laser spectrometers that use lower-power consuming diode lasers often operate at near-IR wavelength ranges, where trace gas molecules may exhibit lower absorbance as compared to the IR range. Additionally, conventional solutions employ complex closed optical chambers (e.g., closed gas cells) with sophisticated mechanisms that sample and drive ambient air into the chamber while maintaining the chamber at nearly constant temperature and pressure, which may be below ambient temperature and pressure. This adds further complexity, size, and weight to the laser spectrometer, which drive up its power usage and cost.

Thus, what is desired is a low-cost, low-power, lightweight, portable, laser spectrometer for detecting and/or measuring the concentration of trace gases, and a method of using the same to detect trace gases.

SUMMARY

Aspects of embodiments of the present invention are directed to a low-power, small and portable, tunable laser spectrometer for detection of a trace gas, such as methane, and a method of detecting the trace gas using the same.

Aspects of embodiments of the present invention are directed to providing an open-path laser spectrometer (OPLS) having an open optical path region (e.g., an open-path analysis region) exposed to the ambient atmosphere, and not requiring temperature and/or pressure control.

According to an embodiment of the present invention, there is provided an open-path laser spectrometer for measuring a concentration of a trace gas, the open-path laser spectrometer including: an open-path multi-pass analysis region including a first mirror, a second mirror at a distance and orientation from the first mirror, and a support structure for locating the first and second mirrors; a laser coupled to the open-path multi-pass analysis region and configured to emit light of a wavelength range and to enable a plurality of reflections of the emitted light between the first and second mirrors; a detector coupled to the open-path multi-pass analysis region and configured to detect a portion of the emitted light impinging on the detector and to generate a signal corresponding to a characteristic of the detected portion of the emitted light; and an electronic system coupled to the laser and the detector, and configured to adjust the wavelength range of the emitted light from the laser based on the generated signal, and to measure the concentration of the trace gas based on the generated signal.

The trace gas may exhibit a resonant frequency response in the wavelength range of the emitted light, and other gases in the atmosphere do not exhibit resonant frequency responses in the wavelength range. The trace gas may be methane.

The laser may include a semiconductor laser diode operating in an infrared range. The wavelength range may be from about 3.2 µm to about 3.5 µm.

The open-path multi-pass analysis region may be exposed to the ambient atmosphere. For example, an optical path in the open-path multi-pass analysis region may be at near ambient temperature and at near ambient pressure.

The open-path multi-pass analysis region may include a Herriott cell, wherein the first and second mirrors may be opposing concave mirrors, and wherein the first mirror includes a first hole configured to allow light to enter and/or exit the open-path multi-pass analysis region.

The first hole may be configured to allow the emitted light to enter the open-path multi-pass analysis region, and wherein the second mirror includes a second hole configured to allow the reflected light to exit the open-path multi-pass analysis region.

The open-path laser spectrometer may be configured to utilize a direct laser absorption and/or 2f modulation/demodulation spectrometry techniques.

The electronic system may include a global positioning system (GPS) configured to track a location of the open-path laser spectrometer and to synchronize the location with the generated signal of the detector.

The electronic system may further include a wireless transceiver configured to enable communication between the open-path laser spectrometer and an external device.

The open-path laser spectrometer may have a trace-gas detection sensitivity of about 10 parts per billion (ppb) in 1 second.

The open-path laser spectrometer may be portable and hand-held.

The distance between the first and second mirrors may be between about 8 cm and about 20 cm and a total optical path length of the open-path multi-pass analysis region may be more than 4 m.

The open-path laser spectrometer may further include a thermoelectric cooler (TEC) configured to control a temperature of an emission source of the laser, wherein the electronic system is configured to adjust the wavelength range of the emitted light from the laser by detecting a wavelength shift in a spectrum of the generated signal, and by signaling the TEC to control the temperature of the emission source of the laser.

According to an embodiment of the present invention there is provided a method for measuring a concentration of a trace gas including: providing an open-path laser spectrometer including: an analysis region including a first mirror and a second mirror at a distance from the first mirror; a laser; a detector; and an electronic system, wherein the laser is configured to emit light of a wavelength range toward the second mirror, the emitted light reflecting off of the first and second mirrors a plurality of times before impinging on the detector; exposing the analysis region of the open-path laser spectrometer to the ambient atmosphere; detecting, by the detector, a characteristic of the impinging light, and generating, by the detector, a signal corresponding the detected characteristic of the impinging light; adjusting, by the electronic system, the wavelength range of the emitted light from the laser based on the generated signal; and measuring, by the electronic system, a concentration of the trace gas based on the generated signal.

Exposing the analysis region may include exposing an optical path in a region between the first and second mirrors to an ambient temperature and an ambient pressure.

The trace gas exhibits a resonant frequency response in the wavelength range of the emitted light, and other gases in the atmosphere do not exhibit resonant frequency responses in the wavelength range.

The open-path laser spectrometer may further include a thermoelectric cooler (TEC) configured to control a temperature of an emission source of the laser, wherein adjusting the wavelength range of the emitted light from the laser includes: detecting, by the electronic system, a wavelength shift in a spectrum of the generated signal, and signaling, by the electronic system, the TEC to control the temperature of the emission source of the laser.

BRIEF DESCRIPTION OF THE DRAWINGS

In order to facilitate a fuller understanding of the present invention, reference is now made to the accompanying drawings, in which like elements are referenced with like numerals. These drawings should not be construed as limiting the present invention, but are intended to be illustrative only.

DETAILED DESCRIPTION

The detailed description set forth below in connection with the appended drawings is intended as a description of illustrative embodiments of a system and method for detection of a trace gas in accordance with the present invention, and is not intended to represent the only forms in which the present invention may be implemented or utilized. The description sets forth the features of the present invention in connection with the illustrated embodiments. It is to be understood, however, that the same or equivalent functions and structures may be accomplished by different embodiments that are also intended to be encompassed within the spirit and scope of the present invention. As denoted elsewhere herein, like element numbers are intended to indicate like elements or features.

The present invention relates to a system and method for detection of a trace gas utilizing a compact, low-cost, low-power, tunable laser spectrometer having an open-path multi-pass analysis region (e.g., an open-path multi-pass optical cell). The laser light source may be a low-power semiconductor laser diode radiating in a narrowband of the infrared range of the electromagnetic spectrum, where the trace gas has characteristic absorption (e.g., about 3.2 μm to about 3.5 μm wavelength range for methane detection). In an embodiment, the open-path multi-pass analysis region may be exposed to the ambient atmosphere, and, for example, may not be enclosed in a walled housing. The open-path tunable laser spectrometer may be compact and lightweight, while exhibiting high detection sensitivity in the presence of mechanical disturbances and temperature variations.

Figure 1:
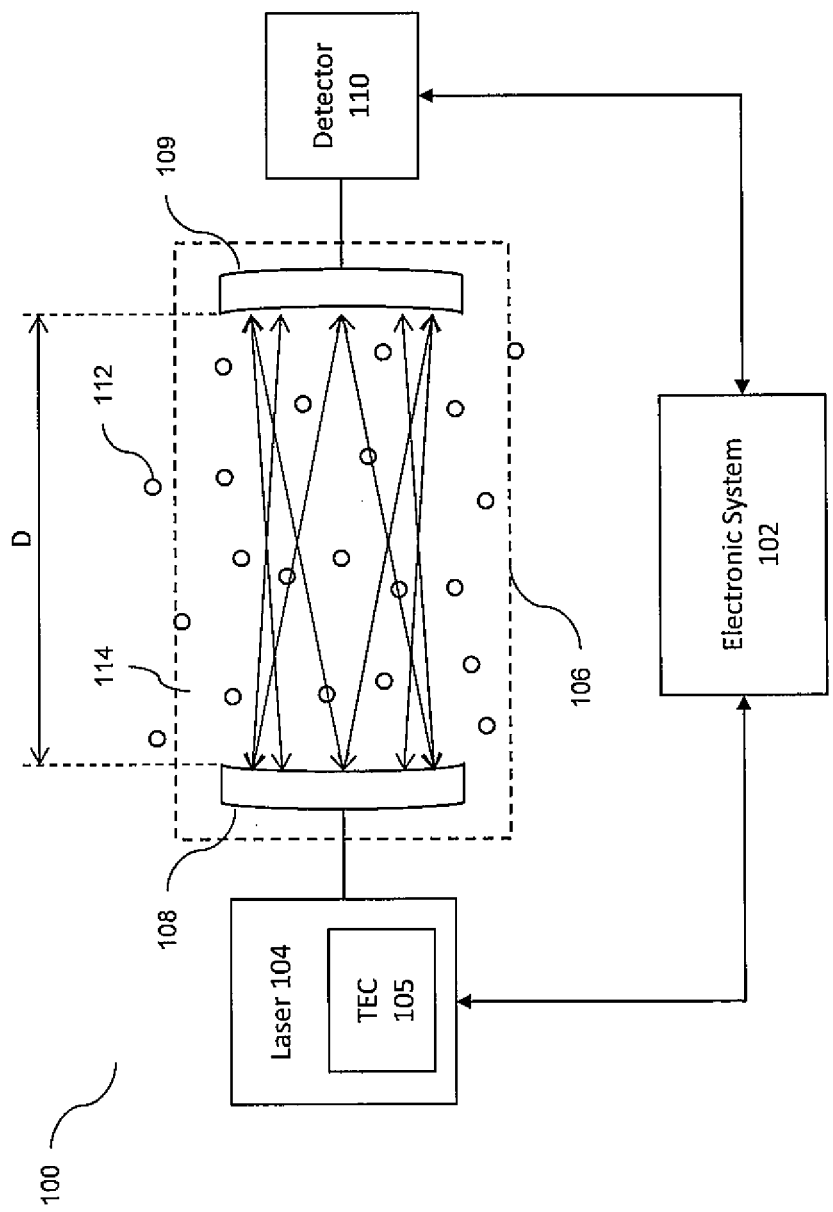
FIG. 1 is a block diagram illustrating an open-path laser spectrometer (OPLS) for detecting a trace gas utilizing an open-path analysis region, according to an illustrative embodiment of the present invention.

FIG. 1 is a block diagram illustrating an open-path laser spectrometer (OPLS) 100 for detecting a trace gas utilizing an open-path analysis region (e.g., open-path optical cell) 106, according to an illustrative embodiment of the present invention. In an embodiment, the OPLS 100 includes an electronic system 102, a laser 104, which includes a thermoelectric cooler (TEC) 105, an analysis region 106 including first and second mirrors 108/109, and a detector 110.

According to an embodiment, the electronic system 102 may control the laser 104 by, for example, driving/exciting the laser 104 and/or controlling the laser temperature and may control the detector 110 and process the signal generated by the detector 110 to determine the concentration of a trace gas (e.g., methane) 112 in an atmosphere 114. The electronic system 102 may further transmit the collected information from the detector 110 and/or the processed information to an external device.

In an embodiment, the laser 104 includes a light emission source, such as a semiconductor laser (e.g., a semiconductor laser diode, a vertical-cavity surface-emitting laser (VC- SEL), interband cascade (IC) lasers, and/or the like), emitting light of a narrowband within a wavelength range in which the trace gas 112 exhibits a relative high light absorption as compared to other gases in the atmosphere 114. Thus, the wavelength range is chosen such that the frequency response of the trace gas 112 of interest exhibits a resonance, which is distinguished from the frequency response of other gas molecules in the surrounding atmosphere 114. For example, if the trace gas 112 is methane, the wavelength range may be from about 3.1 μm to about 3.6 μm and the narrowband of emission may be centered at a wavelength between about 3.25 μm and about 3.38 μm (e.g., about 3.27 μm). The laser 104 may be tunable and, in the example of methane detection, may have a spectral tuning range of about 0.6 cm$^{-1}$ (e.g., from about 3057.4 cm$^{-1}$ to about 3058 cm$^{-1}$, where methane absorbs strongly but other molecules, such as water and carbon dioxide, do not).

According to an embodiment, the laser 104 includes a TEC 105 for temperature control to maintain (or improve) light emission output levels and wavelength integrity. The electronic system 102 tunes the laser 104 to near an absorption line of the trace gas 112 by controlling the injected DC current and by driving the TEC 105 to regulate the temperature of the light emission source.

In an embodiment, the drive current of the laser 104 may be modulated by the electronic system 102 in order to improve the absorption sensitivity and accuracy of the OPLS 100. The electronic system 102 may introduce a sinusoidal modulation current having a frequency f (e.g., 10 MHz) on top of the DC drive current, which may shift the detection band to a high-frequency region where the 1/f laser noise is reduced (e.g., minimized). In some examples, the frequency f may be in the kHz, MHz, or even GHz ranges depending on, for example, the absorption linewidth of the trace gas 112, the detection bandwidth of the detector 110, and/or the desired detection sensitivity of the OPLS 100.

The light emission source may consume little power, for example, a semiconductor laser diode may operate at less than 200 mA of current and less than 2.5 V voltage, thus enabling the open-path laser spectrometer (OPLS) 100 to be powered by an off-the-shelf battery, such as a AA or AAA battery, which may allow for better portability of the OPLS 100.

The laser 104 may further include a mechanical housing with optics configured to direct the laser light (e.g., the light beam) into the analysis region 106.

In an embodiment, the analysis region 106 is structured as an open-path multi-pass absorption cell, such as a Herriott cell, and includes a support structure for maintaining (e.g., locating) the first and second mirrors 108/109 a distance D apart. The distance D may be between about 8 cm to about 20 cm (e.g., D may be about 15.4 cm). The support structure may include two mirror holders and two or more connecting rods. In an example, the open-path multi-pass absorption cell includes more than two mirrors (e.g., three mirrors, as in a White cell).

According to an embodiment, the analysis region 106 is not encased in an enclosure and the analysis region 106 has free access to the ambient atmosphere. Thus, the analysis region 106 and the volume between the first and second mirrors 108/109 are at (e.g., are exposed to) the ambient temperature and pressure. The open-path structure of the analysis region 106 obviates the need for a pump, which may have been a necessary component in some conventional laser spectrometers.

The first and second mirrors 108/109 may be opposing concave mirrors (e.g., facing spherical confocal mirrors). In one example, the opposing mirrors 108 may have a diameter between about 1 cm to about 7.5 cm (or, e.g., between about 2 cm to about 5 cm, such as about 2.5 cm), and a radius of curvature between 1 cm to about 70 cm (or, e.g., between about 10 cm to about 50 cm, such as about 34 cm). In an embodiment, the opposing mirrors 108/109 include a substrate material having a low (e.g., very low) coefficient of thermal expansion (e.g., having a thermal expansion coefficient lower than borosilicate glass), such as a lithium aluminosilicate glass-ceramic material, which allow the mirrors 108/109 to retain their figures in the presence of ambient temperature changes. However, in an example, weight considerations may trump temperature sensitivity concerns and the substrate material may be chosen from a group of lightweight materials such as Aluminum.

The mirrors 108/109 may include a coating of a reflective material, such as gold, silver, aluminum, polished metal, and/or the like. The reflective coating may exhibit greater than 95% reflection at wavelength of about 3.3 μm. The coating may also be reflective in the visible range of the light wavelength spectrum to allow for easy alignment.

In an embodiment, a hole may be created in one or more of the mirrors 108/109 to enable the emitted light beam from the laser 104 to enter and exit the analysis region 106. In one example, the light beam enters the analysis region 106 from one side and exits from another side. Alternatively, the light beam may enter and exit the analysis region 106 from a same side. The hole may be created by, for example, machining a physical hole through the one or more mirrors 108/109, or by removing a portion of the reflective coating on the one or more mirrors 108/109 in the case of mirror substrate materials that are transparent to the laser wavelength range.

The open-path analysis region 106 (e.g., the open-path multi-pass absorption cell) may be configured to allow multiple reflections (e.g., traversals) of the emitted light beam between the first and second mirrors 108/109 before finally impinging on the detector 110, thus offering an effective optical pathlength far greater than the distance D. The number of traversals, and thus, the effective optical pathlength, may be controlled by adjusting the separation distance D between the first and second mirrors 108/109 and/or the diameter of the opposing mirrors 108/109. In one example, the open-path analysis region 106 permits 27 traversals for a total optical pathlength of more than 4 m. As the optical pathlength increases, there is greater opportunity for the molecules of the trace gas 112 to interact with (and absorb a portion of the energy of) the reflecting light beam as it traverses the open-path cell, thus detection sensitivity may be improved (e.g., increased).

An embodiment in which the analysis region 106 has only two mirrors that are spaced close to one another may be less susceptible to mechanical disturbances, and thus, permit higher detection sensitivity and portability, than an embodiment in which more than two mirrors are used or in which the mirrors are spaced further apart.

The detector 110 may include a photodetector (e.g., a semiconductor detector or a photovoltaic photodetector), which may receive the reflected light beam through a hole in the second mirror 109, which is opposite from the laser 104, or through a same or different hole in the first mirror 108, which is adjacent to the laser 104. The photodetector may be small, e.g., about 1 mm in size, and may be integrated with a lens (e.g., a hemispherical or hyperhemispheric lens) and/or optical filters for improved (e.g., increased) acceptance angle and saturation level. When a reflected light beam impinges on the photodetector, the detector 110 generates a signal corresponding to a characteristic of the impinging light (e.g., generates a current signal proportional to the intensity of the impinging light), which the detector 110 transmits to the electronic system 102 for further processing. The detector 110 may include a preamplifier, such as a transimpedance preamplifier having an adjustable cut-off frequency, for converting and amplifying the generated signal (e.g., converting the generated current signal to an amplified voltage signal) before transmitting it to the electronic system 102. Keeping the photodetector and the preamplifier close together may improve (e.g., increase) the signal-to-noise ratio (SNR) of the detector 110.

According to an embodiment, the detector 110 employs a direct absorption and/or a modulated detection scheme, such as 2f, 4f, and/or the like, where f represents a modulation frequency at the laser 104. In an embodiment, the preamp may generate, and subsequently transmit to the electronic system 102, one or more signals representing a modulated signal (e.g., a 2f signal) and/or a non-modulated signal (when direct absorption is employed).

In an embodiment, the OPLS 100 further includes a power regulator for inputting power from a direct-current (DC) power source, such as a battery, and generating one or more output voltages corresponding to the operating voltages of the various components of the OPLS 100. The power regulator may be physically separated (e.g., isolated) from the electronic system 102 and the detector 110 to reduce (e.g., minimize) noise and improve (e.g., increase) the detection sensitivity of the OPLS 100.

Accordingly, in an embodiment of the present invention, the OPLS 100 is compact (e.g., less than 18 cm in length), lightweight (e.g., weighing less than 300 gr), has low power consumption (e.g., less than 2 W), and is able to achieve a high detection sensitivity (e.g., about 10 ppb per second), while exhibiting mechanical robustness and low susceptibility to temperature variation. In some embodiments, the OPLS 100 may be configured as a hand-held spectrometer, which may be carried by a human user, and/or may be configured to mount to a vehicle, such as an unmanned aerial vehicle (UAV) platform.

While the numerical examples provided above were primarily related to detection of methane gas, by changing the center wavelength of the laser 104, and reconfiguring the analysis region 106 by, for example, readjusting the distance D between the opposing mirrors 108/109, modifying the diameter of mirrors 108/109, and/or modifying the coating material of the mirrors 108/109, the OPLS 100 may be adapted to detect a different trace gas, such as carbon dioxide ($CO_2$) or water vapor ($H_2O$) in the atmosphere 114.

Figure 2:
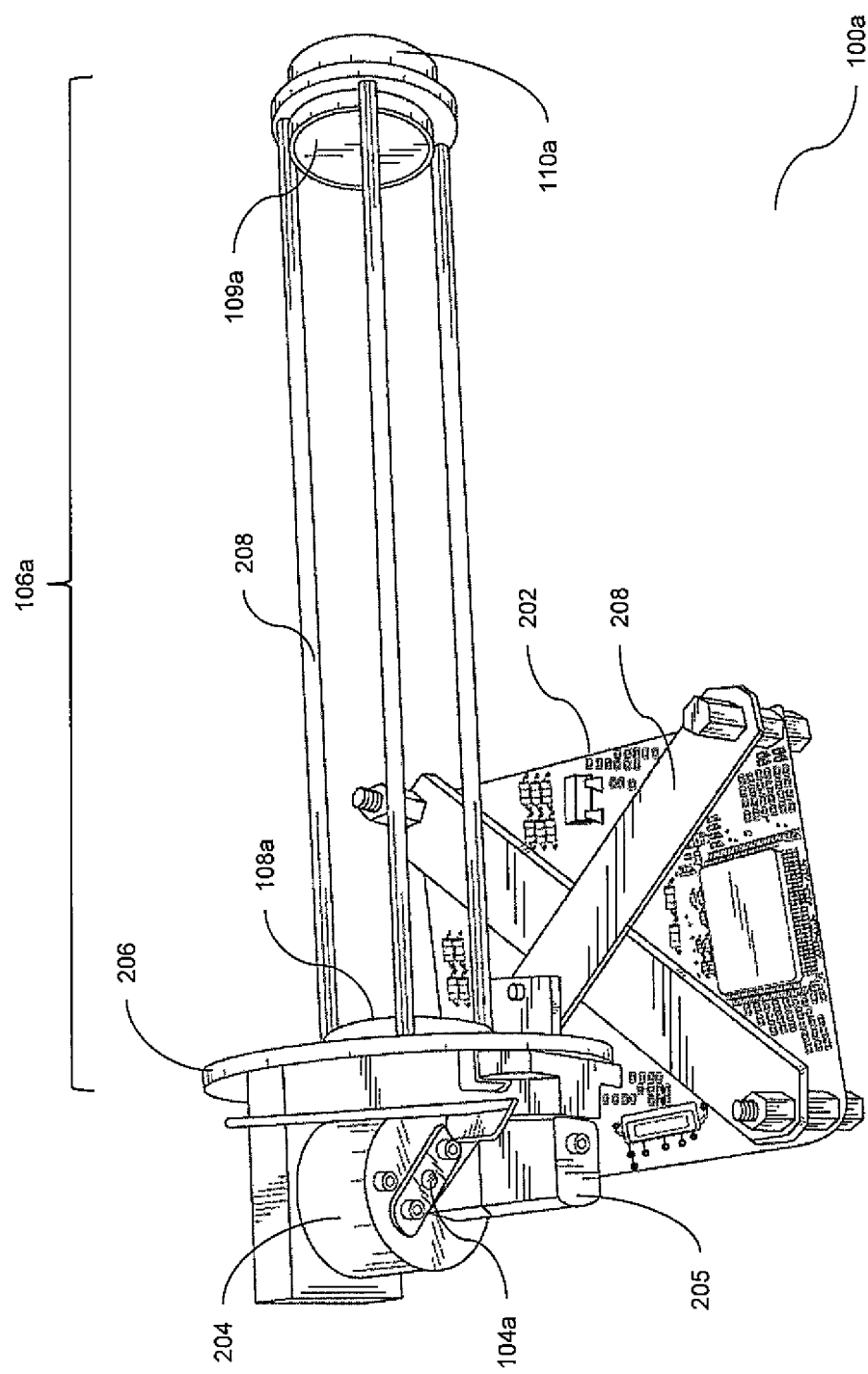
FIG. 2 is a schematic diagram illustrating a perspective view of the OPLS of FIG. 1, according to an illustrative embodiment of the present invention.

FIG. 2 is a schematic diagram illustrating a perspective view of the OPLS 100a of FIG. 1, according to an illustrative embodiment of the present invention.

According to an embodiment, the OPLS 100a includes a microcontroller board 202, which includes an implementation of the electronic system 102, a laser housing 204 for housing the light emission source of the laser 104, optical elements 205 for directing the light beam from the light emission source toward the first and second mirrors 108a/109a, a mounting board 206 for coupling the analysis region 106a to the laser housing 204, connecting rods for coupling the first and second mirrors 108a/109a together and to the mounting board 206, and a connecting scaffold 210 for coupling the microcontroller board 202 to the mounting board 206 and the analysis region 106a. According to an embodiment, the laser housing 204 is coupled to a first mirror 108a and the detector 110a is coupled to a second mirror 109a. The open-path volume between the first and second mirrors 109a is not encapsulated in a housing (e.g., is uncovered) and is freely exposed to the ambient atmosphere 114.

In an embodiment, the optical elements 205 are configured to direct the light beam emanating from the laser 104a through a hole formed in the first mirror 108a and toward the second mirror 109b. In another embodiment, the light emission source of the laser 104 may be coupled to (e.g., directly coupled to) the first mirror 108a in a manner such that no optical elements 205 are needed to direct its light beam toward the second mirror 109a. Such an embodiment, which does not utilize the optical elements 205, may be more robust and less susceptible to mechanical disturbances than an embodiment utilizing the optical elements 205 for directing the path of the laser light beam.

FIGS. 3A-3E are schematic diagrams illustrating the laser, analysis region, and the concave lenses of the OPLS of FIG. 1, according to illustrative embodiments of the present invention.

Figure 3C:
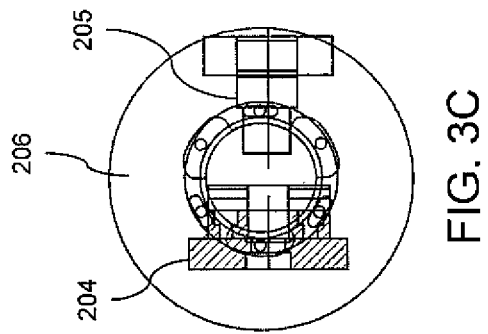
FIGS. 3A-3E are schematic diagrams illustrating the laser, analysis region, and the concave lenses of the OPLS of FIG. 1, according to illustrative embodiments of the present invention.
Figure 3A:
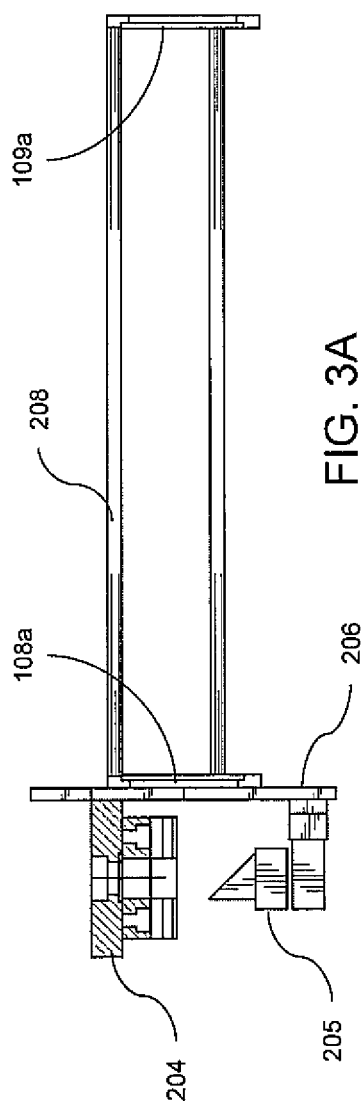
Figure 3B:
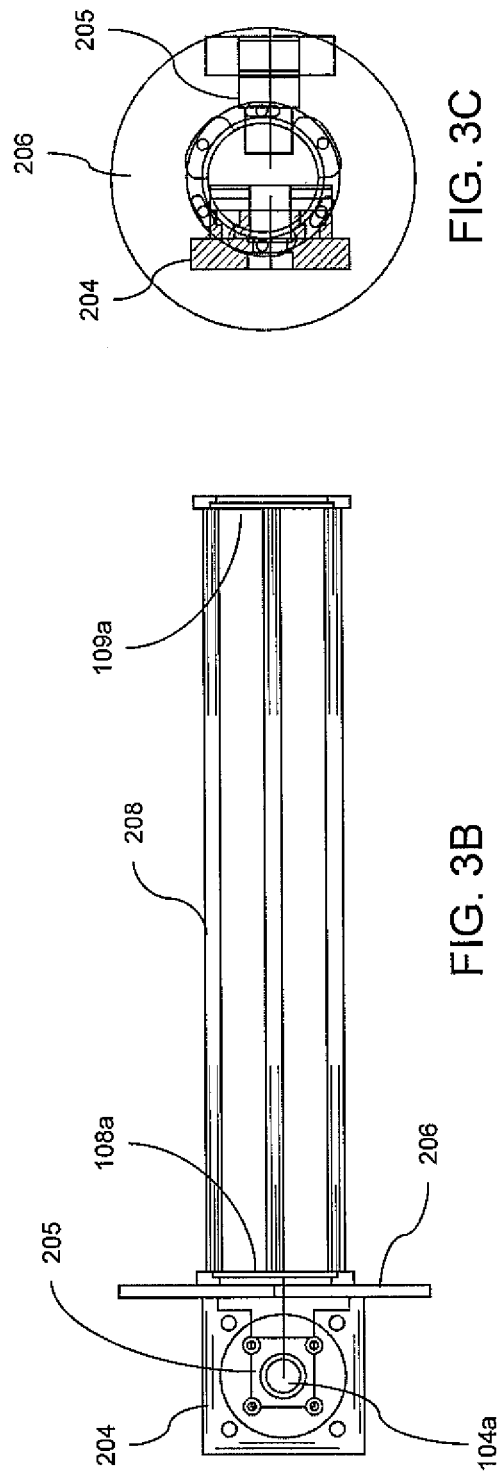

FIGS. 3A, 3B, and 3C are top, side, and front views, respectively, of the laser housing 204, the optical elements 205, the mounting board 206, and the connecting rods 208, according to an embodiment of the present invention. The optical elements 205 may include, for example, an astigmatic collimating optic with adjustable focus and an about 90° turning mirror for directing the laser beam into the analysis region 106a.

Figure 3E:
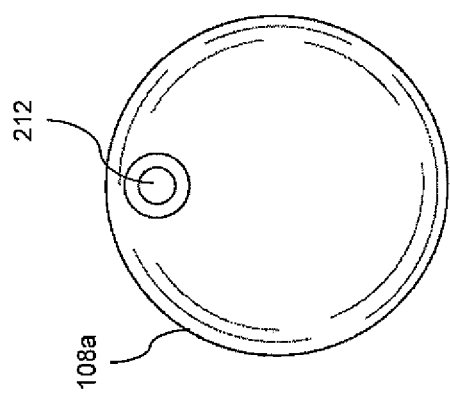
Figure 3D:
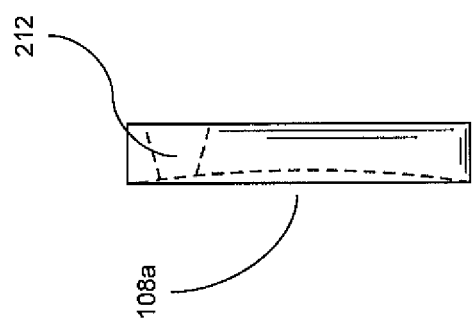

FIGS. 3D and 3E are side and front views, respectively, of the first mirror 108a, according to an embodiment of the present invention. In an embodiment, the first mirror 108a includes a hole 212, which allows the light beam from the laser 104 to pass through the first mirror 108a and toward the second mirror 109a. The first mirror 108a may have a radius of curvature between 10 cm and 50 cm. In one example, the hole 212 may be positioned 8.9 mm from the center of the first mirror 108a and have an average diameter between about 2.7 mm to about 3.2 mm. The second mirror 109a may include a similar hole for allowing the reflected laser beam to pass through the second mirror 109a and impinge on the detector 110a.

Figure 4:
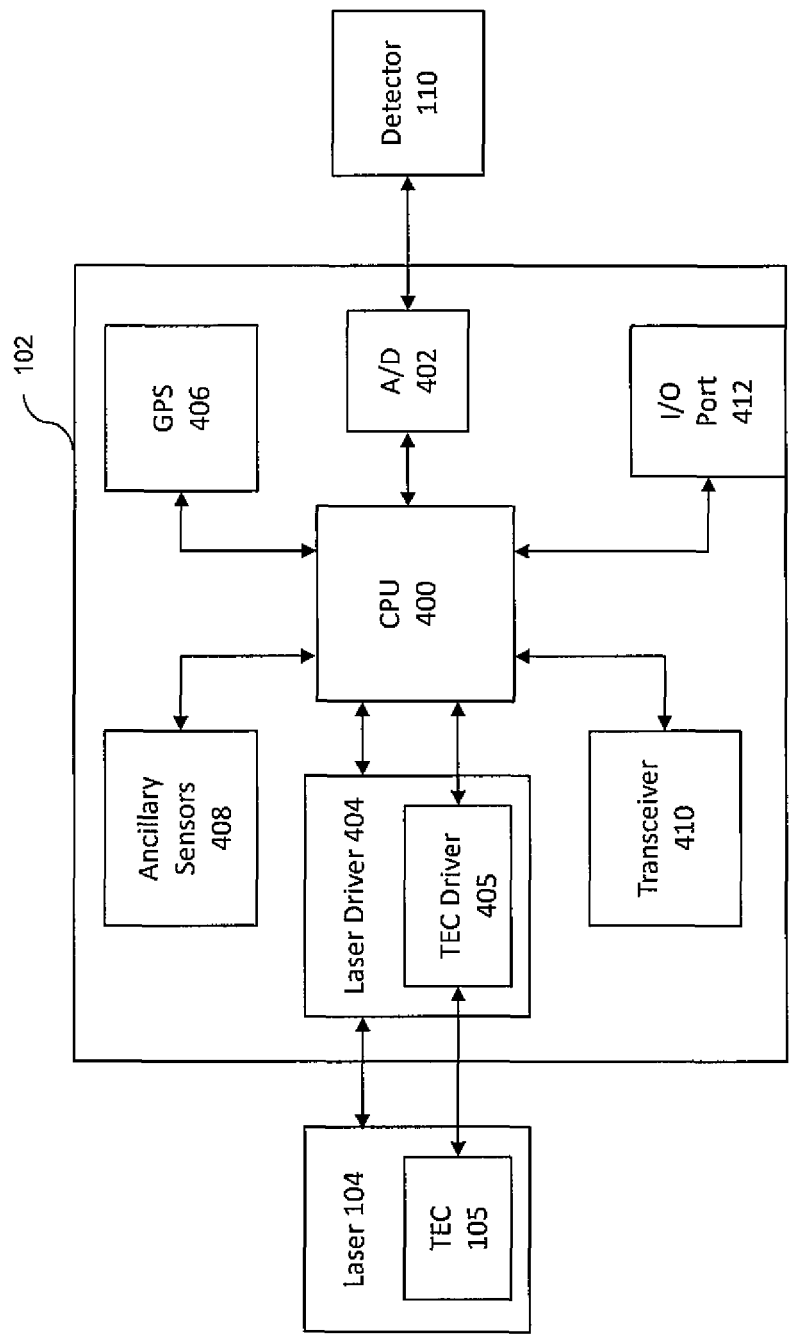
FIG. 4 is a block diagram illustrating the electrical system of the OPLS of FIG. 1, according to an illustrative embodiment of the present invention.

FIG. 4 is a block diagram illustrating the electronic system 102 of the OPLS 100, according to an illustrative embodiment of the present invention. According to an embodiment, the electronic system 102 includes a processor (e.g., central processing unit (CPU)) 400, one or more analog-to-digital converters (A/Ds) 402, a laser driver 404, a global positioning system (GPS) 406, ancillary sensors 408, a transceiver 410, and an input-output (I/O) port 412.

The A/D 402 coupled to the detector 110 may digitize the signal from the detector 110 for processing (e.g., real-time processing) by the processor 400.

The processor 400 utilizes the digitized signal from the detector 110 to determine the concentration of the trace gas. In an example in which the laser drive signal is modulated at a frequency f, the processor 400 may demodulate the digitized signal at 2f, 4f, and/or 6f by utilizing, for example, a lock-in amplifier. In an example in which no modulation was used (as is the case with direct absorption), the processor 400 does not perform demodulation of the detector signal and instead processes the raw data provided by the detector 110. The processor 400 may then average the spectral data acquired from the raw/demodulated data over a period of time (e.g., one second) and compare the result against reference spectral data (e.g., modeled data or spectral data collected in the absence of the trace gas 112) to determine the concentration of the trace gas 112. In so doing, the processor 400 may compare the spectral characteristics of the processed data with those of the reference data (e.g., the modeled data). The spectral characteristics may include, for example, peak amplitude, linewidth, and center wavelength of the averaged spectral data. Further, the processor 400 may control and facilitate communication between the above-mentioned constituent blocks of the electronic system 102.

The laser driver 404 may deliver a preset current to the laser 104 for exciting the laser 104 and producing a light of a preset wavelength. In an embodiment, the electronic system 102 may further include a laser current modulation circuitry to enable modulation (e.g., 2f modulation) of the laser drive current.

The processor 400 may instruct the laser driver 404 to modulate the drive current of the laser 104, or to turn off modulation, depending on whether the OPLS 100 is operating under direct absorption or modulation schemes. In an embodiment, the OPLS 100 may alternate (e.g., periodically alternate) between modulation mode and direct absorption mode. In so doing, the OPLS 100 may utilize the measurement results under direct absorption mode to calibrate the measurement results from modulation mode. For example, direct absorption concentration values may be interleaved with modulation concentration values and the modulation concentration values may be scaled to match the interpolated direct absorption results, which may be more accurate but less precise.

In one example, the laser driver 404 also includes a thermoelectric cooler (TEC) driver 405 for operating a TEC 105 inside the laser 104 to regulate its temperature and to properly tune the light emission source (e.g., the semiconductor laser) of the laser 104. Inadequate temperature control may lead to changes in temperature of the light emission source, which, in turn, may adversely affect the spectra of the emitted light beam (by, e.g., shifting its center wavelength), and hence reduce absorption sensitivity and/or measurement accuracy. In one example, the processor 400 monitors the temperature readings from a temperature sensor on (but external to) the light emission source, and instructs the TEC driver 405 to compensate for any drifts in temperature.

According to an embodiment of the present invention, in addition to, or in lieu of, monitoring the temperature at the light emission source, the processor 400 detects temperature changes inside of the light emission source by monitoring shifts in spectra (e.g., shifts in center wavelengths of the spectra) of the detected light, which has interacted with a trace gas. Shifts beyond a predetermined noise threshold may prompt the processor 400 to signal the TEC 105 to adjust the temperature of the light emission source of the laser 104 by an amount sufficient to compensate for the shift in spectra (e.g., shift the emission wavelength versus current of the laser 104 back to its original position). In an embodiment, the emission wavelength versus current of the laser may be determined by real-time processing of the data, which assesses the linecenter(s) of the trace gas resonance(s) in relation to the laser current. According to an embodiment, the temperature control feedback may be dampened by an algorithm that prevents rapid changes to the laser temperature control in the event that the real-time processing is corrupted by data anomalies such as blockage of the light.

In an embodiment, the OPLS 100 is equipped with a number of sensors, which may enable the OPLS 100 to be situationally aware. For example, the GPS 406 may track the geographical location of the OPLS 100 and automatically synchronize the location information with any other data collected/processed by the OPLS 100. Thus, the OPLS 100 may be utilized to construct a spatial map of the trace gas concentrations. Further, the ancillary sensors 408 may include an integrated pressure sensor and/or a temperature sensor for measuring ambient pressure and/or temperature of the atmosphere 114. The temperature and pressure readings from the ancillary sensors 408 may be used by the processor 400 in determining the concentration of the trace gas 112 based on the data received from the detector 110.

In an embodiment in which high measurement accuracy is desired, as may be the case, for example, when using the OPLS 100 to measure concentration variations in remote geographical locations where the changes in trace gas concentrations may be very small (e.g., on the order of tens of parts-per-billion over several seconds), the processor 400 may rely on ambient temperature readings from a temperature sensor (e.g., a thermistor) at the analysis region 106 (e.g., fastened to a connecting rod holding the mirrors 108/109). The temperature readings of such a sensor may more accurately represent the temperature of the molecules of the trace gas 112 probed by the laser light beam than the readings of the temperature sensors of the ancillary sensors 408.

Through the transceiver 410, the OPLS 100 may be able to communicate with an external device. For example, the transceiver 410 may include a Bluetooth transceiver capable of wirelessly transmitting geo-location and sensed data to a mobile phone, a laptop, and/or a central server. Further, the transceiver 410 may permit wired serial communication with the external device by utilizing, for example, the recommended standard 232 (RS-232) and/or the transistor-to-transistor logic (TTL) serial communication protocols. The I/O port 412 may enable the OPLS 100 to read/write data onto a portable media, such as a secure digital (SD) card (e.g., a microSD disc).

Other embodiments of the electronic system 102 are within the scope and spirit of the present invention. For example, the functionality described above with respect to the electronic system 102 can be implemented using software, hardware, firmware, hardwiring, or combinations thereof. One or more computer processors operating in accordance with instructions may implement the function of the electronic system 102 in accordance with the present invention as described above. It is within the scope of the present invention that such instructions may be stored on one or more non-transitory processor readable storage media (e.g., a magnetic disk, non-volatile random-access memory, phase-change memory or other storage medium). Additionally, modules implementing functions may also be physically located at various positions, including being distributed such that portions of functions are implemented at different physical locations.

Figure 5:
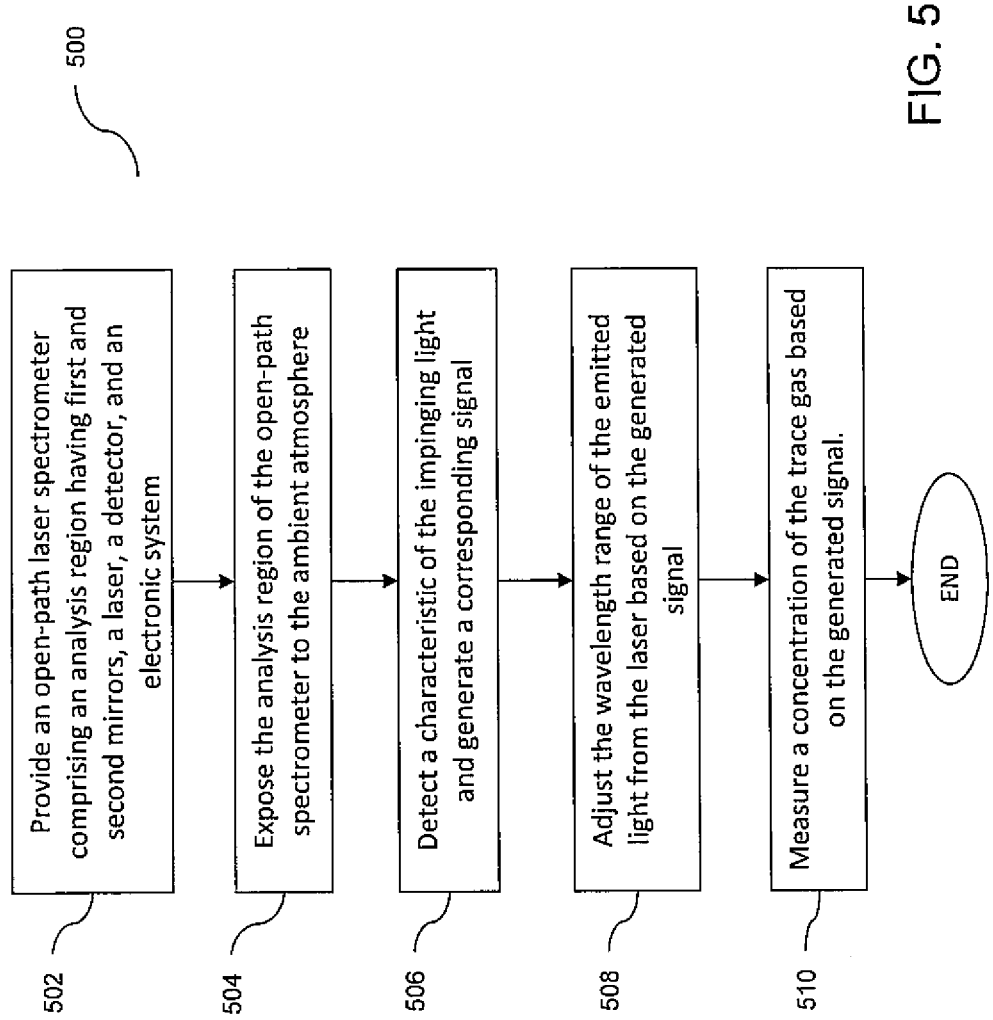
FIG. 5 is a flow diagram illustrating a process for detection of a trace gas, according to an illustrative embodiment of the present invention.

FIG. 5 is a flow diagram illustrating a process 500 for detection of a trace gas 112, according to an illustrative embodiment of the present invention.

At act 502, the open-path laser spectrometer (OPLS) 100 illustrated in FIG. 1 is provided, which includes an analysis region 106 having first and second mirrors 108/109 at a distance D from each other, a laser 104 having a light emission source and a thermoelectric cooler (TEC) 105 for controlling the temperature of the light emission source, a detector 110, and an electronic system 102. The laser 104, which is adjacent to the first mirror 108, emits a light of a wavelength range (e.g., a nearly fixed linewidth) toward the second mirror 109. The emitted light beam may reflect off of the first and second mirrors 108/109 a plurality of times before impinging on the detector 110, which may be adjacent to the second mirror 109.

At act 504, the analysis region 106 of the OPLS 100 is exposed to the ambient atmosphere. Accordingly, the analysis region 106 and the volume between the first and second mirrors 108/109 is at (e.g., is exposed to) the ambient temperature and pressure.

At act 506, the detector 110 detects a characteristic (e.g., the intensity) of the impinging light beam and generates an electrical signal corresponding to the detected characteristic of the impinging light.

At act 508, the electronic system 102 adjusts (e.g., tunes) the wavelength range of the emitted light beam from the laser 104 based on the generated signal. The electronic system 102 may adjust the wavelength range (e.g., shift a center wavelength of the wavelength range) by detecting a wavelength drift in the spectrum of the generated signal and signaling the TEC 105 to control the temperature of the light emission source of the laser 104 to compensate for the wavelength drift. According to an embodiment, the electronic system 102 adjusts (e.g., tunes) the wavelength range of the emitted light beam by further detecting temperature changes based on readings from the temperature sensor on (but external to) the light emission source of the laser 104.

At act 510, a concentration of the trace gas 112 is measured based on the generated signal. The electronic system 102 calculates one or more spectral characteristics of the generated signal, such as peak amplitude, linewidth, and center wavelength, and compares the result(s) against reference data (e.g., modeled data), to determine the concentration of the trace gas 112.

The present invention is not to be limited in scope by the specific embodiments described herein. Indeed, other various embodiments of and modifications to the present invention, in addition to those described herein, will be apparent to those of ordinary skill in the art from the foregoing description and accompanying drawings. Thus, such other embodiments and modifications are intended to fall within the scope of the present invention. Further, although the present invention has been described herein in the context of a particular implementation in a particular environment for a particular purpose, those of ordinary skill in the art will recognize that its usefulness is not limited thereto and that the present invention may be beneficially implemented in any number of environments for any number of purposes. Accordingly, the claims set forth below should be construed in view of the full breadth and spirit of the present invention as described herein.

What is claimed is:

1. An open-path laser spectrometer for measuring a concentration of a trace gas, the open-path laser spectrometer comprising:
    an open-path multi-pass analysis region comprising a first mirror, a second mirror at a distance and orientation from the first mirror, and a support structure for locating the first and second mirrors;
    a laser coupled to the open-path multi-pass analysis region and configured to emit light of a wavelength range and to enable a plurality of reflections of the emitted light between the first and second mirrors;
    a detector coupled to the open-path multi-pass analysis region and configured to detect a portion of the emitted light interacting with the trace gas and impinging on the detector and to generate a return signal corresponding to a characteristic of the detected portion of the emitted light; and
    an electronic system coupled to the laser and the detector, wherein the electronic system:
        monitors a spectrum of the generated return signal to determine a shift in a resonance line-center of the trace gas with respect to an injected laser current, as compared to an initial resonance line-center of the trace gas with respect to the injected laser current;
        adjusts a temperature of the laser, based on the determined shift, to return the resonance line-center of the trace gas with respect to the injected laser current back to the initial resonance line-center of the trace gas with respect to the injected laser current; and
        measures the concentration of the trace gas based on the generated return signal.

2. The open-path laser spectrometer of claim 1, wherein the trace gas is methane.

3. The open-path laser spectrometer of claim 1,
    wherein the trace gas exhibits a resonant frequency response in the wavelength range of the emitted light, and
    wherein other gases in the atmosphere do not exhibit resonant frequency responses in the wavelength range.

4. The open-path laser spectrometer of claim 1, wherein the laser comprises a semiconductor laser diode operating in an infrared range.

5. The open-path laser spectrometer of claim 1, wherein the wavelength range is from about 3.2 µm to about 3.5 µm.

6. The open-path laser spectrometer of claim 1, wherein the open-path multi-pass analysis region is exposed to the ambient atmosphere.

7. The open-path laser spectrometer of claim 1, wherein an optical path in the open-path multi-pass analysis region is at near ambient temperature and at near ambient pressure.

8. The open-path laser spectrometer of claim 1,
    wherein the open-path multi-pass analysis region comprises a Herriott cell,
    wherein the first and second mirrors are opposing concave mirrors, and
    wherein the first mirror comprises a first hole configured to allow light to enter and/or exit the open-path multi-pass analysis region.

9. The open-path laser spectrometer of claim 8,
    wherein the first hole is configured to allow the emitted light to enter the open-path multi-pass analysis region, and
    wherein the second mirror comprises a second hole configured to allow the reflected light to exit the open-path multi-pass analysis region.

10. The open-path laser spectrometer of claim 1, wherein the open-path laser spectrometer is configured to utilize a direct laser absorption and/or 2f modulation/demodulation spectrometry techniques.

11. The open-path laser spectrometer of claim 1, wherein the electronic system comprises a global positioning system (GPS) configured to track a location of the open-path laser spectrometer and to synchronize the location with the generated return signal of the detector.

12. The open-path laser spectrometer of claim 1, wherein the electronic system further comprises a wireless transceiver configured to enable communication between the open-path laser spectrometer and an external device.

13. The open-path laser spectrometer of claim 1, wherein the open-path laser spectrometer has a trace-gas detection sensitivity of about 10 parts per billion (ppb) in 1 second.

14. The open-path laser spectrometer of claim 1, wherein the open-path laser spectrometer is portable and hand-held.

15. The open-path laser spectrometer of claim 1, wherein the distance between the first and second mirrors is between about 8 cm and about 20 cm and a total optical path length of the open-path multi-pass analysis region is more than 4 m.

16. The open-path laser spectrometer of claim 1, further comprising a thermoelectric cooler (TEC) configured to control a temperature of an emission source of the laser,
    wherein the electronic system is configured to adjust the temperature of the laser by signaling the TEC to control the temperature of the emission source of the laser to compensate for the determined shift in the resonance line-center of the trace gas with respect to the injected laser current.

17. A method for measuring a concentration of a trace gas comprising:
    providing an open-path laser spectrometer comprising:
        an analysis region comprising a first mirror and a second mirror at a distance from the first mirror;
        a laser;
        a detector; and
        an electronic system,
            wherein the laser is configured to emit light of a wavelength range toward the second mirror, the emitted light reflecting off of the first and second mirrors a plurality of times before impinging on the detector;
    exposing the analysis region of the open-path laser spectrometer to the ambient atmosphere;
    detecting, by the detector, a characteristic of a portion of the emitted light interacting with the trace gas and impinging on the detector, and generating, by the detector, a return signal corresponding to the detected characteristic of the impinging light;
    monitoring, by the electronic system, a spectrum of the generated return signal to determine a shift in a resonance line-center of the trace gas with respect to an injected laser current, as compared to an initial resonance line-center of the trace gas with respect to the injected laser current;
    adjusting, by the electronic system, a temperature of the laser, based on the determined shift, to return the resonance line-center of the trace gas with respect to the injected laser current back to the initial resonance line-center of the trace gas with respect to the injected laser current; and
    measuring, by the electronic system, a concentration of the trace gas based on the generated return signal.

18. The method of claim 17, wherein exposing the analysis region comprises exposing an optical path in a region between the first and second mirrors to an ambient temperature and an ambient pressure.

19. The method of claim 17,
    wherein the trace gas exhibits a resonant frequency response in the wavelength range of the emitted light, and
    wherein other gases in the atmosphere do not exhibit resonant frequency responses in the wavelength range.

20. The method of claim 17, wherein the open-path laser spectrometer further comprises a thermoelectric cooler (TEC) configured to control a temperature of an emission source of the laser,
    wherein adjusting the temperature of the laser comprises:
        signaling, by the electronic system, the TEC to control the temperature of the emission source of the laser to compensate for the determined shift in the resonance line-center of the trace gas with respect to the injected laser current.

* * * * *